United States Patent [19]

Hinz

[11] 4,179,811
[45] Dec. 25, 1979

[54] FRONTAL MOUTH PLATE FOR ORTHODONTIC PROPHYLAXIS AND EARLY TREATMENT OF DENTAL ANOMALIES

[76] Inventor: Rolf Hinz, Körnerstrasse 6, 4690 Herne, Fed. Rep. of Germany

[21] Appl. No.: 544,371

[22] Filed: Jan. 27, 1975

[30] Foreign Application Priority Data

Jan. 29, 1974 [DE] Fed. Rep. of Germany ... 7402919[U]

[51] Int. Cl.² ............................................. A61C 7/00
[52] U.S. Cl. ...................................................... 433/6
[58] Field of Search ................ 32/14 B; 128/136, 137

[56] References Cited

U.S. PATENT DOCUMENTS

| 885,196 | 4/1908 | Steil | 128/136 |
|---|---|---|---|
| 2,543,432 | 2/1951 | Boxer | 220/337 |
| 2,822,612 | 2/1958 | Strickler | 32/14 B |

*Primary Examiner*—Robert Peshock
*Attorney, Agent, or Firm*—Andrus, Sceales, Starke & Sawall

[57] ABSTRACT

A frontal mouth plate is more sharply curved in its middle than at its ends so as to accommodate normal teeth position and provide prophylactic effects to infants. A holding ring is provided on the plate which is separable for cleaning purposes.

2 Claims, 5 Drawing Figures

FRONTAL MOUTH PLATE FOR ORTHODONTIC PROPHYLAXIS AND EARLY TREATMENT OF DENTAL ANOMALIES

This invention concerns a frontal mouth plate for orthodontic prophylaxis and early treatment of tooth position and jaw anomalies, the convex side of which presents a one piece extension for a movable holder.

BACKGROUND OF THE INVENTION

Such anomalies arise in infancy mainly through sucking by the child on the thumb, on fingers, or on sucking bodies. Frontal mouth plates cure this sucking habit. They are carried between the lips and the rows of teeth in the mouth. Injurious sucking is thereby prevented. Additionally, the carrying of the frontal mouth plate operates prophylactically. The training of the tooth position is thereby achieved and jaw anomalies averted. Finally, through the sucking action occurring during the wearing of the frontal mouth plate in infancy, an orthodontic effect on deformed deciduous teeth can be obtained, in which, through lip pressure and sucking of the apparatus against the teeth rows of the denture, tooth position and jaw anomalies are controlled as a form of early treatment.

Known frontal mouth plates are specially made and fitted to the respective patient. These apparatuses are, however, expensive and, according to the habits of the patients, frequently only with difficulty realize intended result.

Further it is known to employ prefabricated frontal mouth plates (cf. the paper of E. Schonherr: Report Regarding 10 Years Experience with Frontal Mouth Plates, in "Deutsche Stomatogie", Volume 21, March 1971, No. 3, Pages 217-223). Such frontal mouth plates are bent on a radius. The radii or curvatures vary according to a standardized progression. With the use of these plates, pressure points are observed. They hurt and disgust the child wearing the plate. To avoid such problems these frontal mouth plates are additionally fitted.

Frontal mouth plates are formed, as a rule, out of a special thermoplastic material. With prefabricated frontal mouth plates, a loop is inserted in a single piece projection of the plate, through which a ring is pulled which hinders the swallowing of the plate. In the projection, and also in the ring, the existing and particularly undercut, surfaces are difficult or impossible to clean and form breeding places for injurious germs.

SUMMARY OF THE PRESENT INVENTION

The present invention is directed to the provision of a new form of a frontal mouth plate which may be fitted without individual adjustment, to any number of patients and also to the formation of such apparatus, the manufacture of which is simplified and the hygiene of which is improved.

The attainment of the foregoing is achieved by a plate which is curved more sharply in the middle of the plate than on the ends of the plate.

With a normal bite, the teeth in the jaw are arranged from the front teeth to the back teeth along a line with decreasing curvature. As a result, the new frontal mouth plate accommodates the desired teeth position from the beginning. It also possesses a better prophylactic effect. Particularly pressure points are eliminated with the wearing of the new plate.

In particular, the curvature of the new plate is approximately elliptical. This elliptical curvature corresponds better to the ideal development of the teeth and the jaw. This elliptical curvature is, in practice, attained through suitably different radii of curvature of the plate. In orthodontic practice the best development is obtained when the radius of curvature of the middle of the plate is proportional to the radius of curvature of the ends of the plate as 3:4, whereby the curvature radii defining surfaces of the plate are uniformly merged together.

Additionally, simplified manufacture of the apparatus is simultaneously obtained because the necessary injection molding die is lighter to work with.

According to the invention, an appropriate extension for the holder arranged in the middle of the plate carries, preferably on two opposite lying surfaces, round projections corresponding to depressions in faces of a slit holding ring. The frontal mouth plate is further simplified because the present ring is slit and the apparatus is formed only out of only two relatively movable connected parts. The improvement in hygiene arises in that the parts, if necessary, can be separated from each other. The projection possesses no undercuts or depressions for its connection with the movable ring, so that the plate and ring by their separation can in every way be thoroughly cleaned.

BRIEF DESCRIPTION OF THE DRAWING

The novelty will be more clearly seen from the following exemplary embodiments.

In the drawing.

DESCRIPTION OF THE PREFERRED EMBODIMENT

Figure 3:
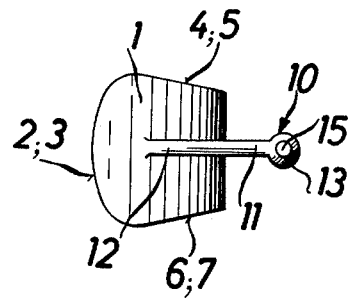
FIG. 3 is a view of the device according to FIG. 1 taken in the direction of the arrow B in FIG. 1.

The frontal mouth plate shown in the Figures consists of a curved plate 1 of constant thickness, the curvature of which in the middle of the plate is sharper than the curvature of the ends of the plate. The ends of plate 1 terminate in lateral edges 2 and 3 which are rounded, as shown, particularly, in FIG. 3. Lateral edges 2 and 3 merge smoothly into top edges 4 and 5 and lower edges 6 and 7.

Section 4 of the upper edge and section 6 of the lower edge adjoining lateral edge 2 form with each other an angle so that the middle of plate 1 is reduced in size. The middle of plate 1 joins sections 4 and 6 with oppositely lying upper and lower edge sections 5 and 7, respectively through radii of curvature 8 and 9.

On the convex side of the middle of plate 1 an extension 10 is formed on the base 11 at which reinforcing rib 12 ends. Reinforcing rib 12 extends toward the ends of the plate and decreases in strength with increasing remoteness from base 11.

Extension 10 contains two side surfaces 13 and 14 on which round projections 15 and 16 are located. Round projections 15 and 16 correspond to depressions 20 and 21 on faces 18 and 19 of the slit holding ring 17 so that the depressions 20, 21 may be pushed over the round projections 15 and 16.

Figure 1:
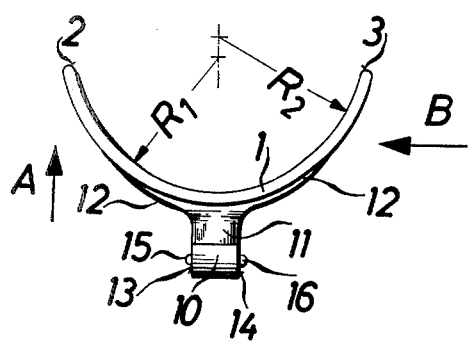
FIG. 1 is a plan view of the frontal mouth plate.
Figure 4:
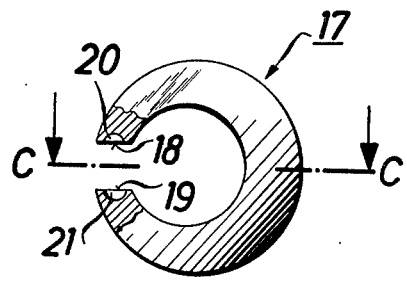
FIG. 4 is a plan view of the separated holding ring of the frontal mouth plate according to FIG. 1.
Figure 5:
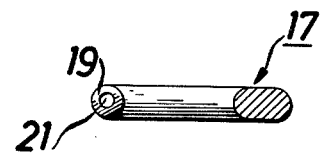
FIG. 5 is a sectional view through the ring of FIG. 4 taken along the line C—C of FIG. 4.
Figure 2:
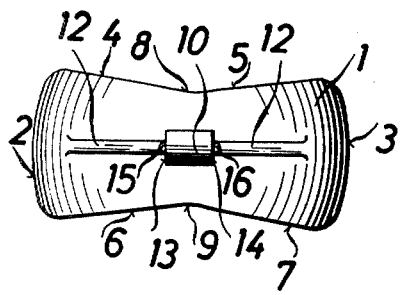
FIG. 2 is a view of the device according to FIG. 1 taken in the direction of the arrow A in FIG. 1.

As particularly shown in FIG. 1, plate 1 is elliptically curved, through which sections constant curvature is approximated. The curvature of the middle of the plate corresponds to the radius of curvature $R^1$ and the curvature of the plate ends corresponds to the radius of curvature $R^2$. In the disclosed embodiment the radius of curvature $R^1$ amounts to 22.5 mm. and the radius of curvature $R^2$ amounts to 30 mm. Such dimensions form a ratio of curvature radii $R^1$ to $R^2$ corresponding to 3:4. The respective curvature radii $R^1$, $R^2$ transition surfaces are merged uniformly together.

I claim:

1. A frontal mouth plate for the early orthodontic prophylaxis of dental anomalies in infants, said plate being generally elongated with a middle portion separating a pair of end portions in the direction of elongation, said plate being elliptically curved in the direction of elongation, the radius of curvature ($R_1$) of the middle portion of the plate about its axis of curvature being proportioned to the radius of curvature ($R_2$) of the end portions about their axis of curvature as 3:4, said middle and end portions being uniformly merged together, said curved plate having a smooth, uninterrupted, concave inner surface which is parallel to said axes of curvature and abuttable with the exterior of the dental structure when the device is placed inside the lips and cheeks, said curved plate having a convex outer surface with an elongated post affixed to the middle portion thereof and extending outwardly therefrom for mounting a movable holder.

2. The device according to claim 1 characterized in that said post mounts a slit holding ring and carries round projections (15, 16) on two opposite lying surfaces (13, 14) spaced apart a distance equal to a small portion of the circumference of the ring, said projections corresponding to depressions (20, 21) in the faces (18, 19) formed in the holding ring by the removal of the small peripheral portion.

* * * * *